United States Patent [19]

Rizkalla

[11] Patent Number: 4,631,348
[45] Date of Patent: * Dec. 23, 1986

[54] PREPARATION OF ACETIC ACID

[75] Inventor: Nabil Rizkalla, River Vale, N.J.

[73] Assignee: The Halcon SD Group, Inc., Little Ferry, N.J.

[ * ] Notice: The portion of the term of this patent subsequent to Apr. 15, 2003 has been disclaimed.

[21] Appl. No.: 746,447

[22] Filed: Jun. 19, 1985

Related U.S. Application Data

[63] Continuation of Ser. No. 431,450, Sep. 30, 1982, abandoned.

[51] Int. Cl.$^4$ .................... C07C 51/12; C07C 51/353; C07C 53/08
[52] U.S. Cl. ..................................... 562/607; 562/519

[58] Field of Search ......................... 562/607, 517, 519

[56] References Cited

U.S. PATENT DOCUMENTS

| | | | |
|---|---|---|---|
| 3,839,428 | 10/1974 | Isogai | 562/517 X |
| 4,194,056 | 3/1980 | Antoniades | 562/517 X |
| 4,323,697 | 4/1982 | Rizkalla | 562/517 X |
| 4,482,497 | 11/1984 | Rizkalla | 260/413 |

*Primary Examiner*—Vivian Garner
*Attorney, Agent, or Firm*—Harold N. Wells

[57] ABSTRACT

Acetic acid is prepared by heating methyl formate in the presence of carbon monoxide by the use of a molybdenum-nickel-alkali metal, a chromium-nickel-alkali metal, or a tungsten-nickel-alkali metal co-catalyst in the presence of an iodide or bromide.

4 Claims, No Drawings 4,631,348

PREPARATION OF ACETIC ACID

This case is a continuation of Ser. No. 431,450, filed Sept. 30, 1982, now abandoned.

This invention relates to the preparation of acetic acid and is more particularly concerned with the production of acetic acid from methyl formate, spacifically the caralytic rearrangement of methyl formate into acetic acid.

The conversion of methyl formate into acetic acid is a known reaction. U.S. Pat. No. 2,508,513, for example, shows a liquid-phase process in which methyl formate is heated in the presence of a carbonyl-forming metal catalyst and halogen, the catalyst being defined as one or more of the iron metals, preferably nickel. The use of nickel iodide hexa-hydrate and nickel carbonyl is exemplified. The process is carried out at a high temperature and, although no yields are reported, it is apparent from the reference to by-products that they are relatively low. U.S. Pat. No. 1,697,109 discloses the vapo-phase conversion of methyl formate into acetic acid, using as catalysts substances which are acetates or capable of forming acetates. Illustrative catalysts of this nature are compounds of copper, tin, lead, zinc and aluminum. No working examples of the process are given. More recently, caralysts based on Group VIII noble metals have been disclosed for this reaction. Thus U.S. Pat. No. 4,194,056 shows the preparation of acetic acid by heating methyl formate in the presence of a soluble rhodium salt and an iodine-containing promoter. Relatively high yields are reported and this patent states that cobalt iodide, cobalt iodide/triphenyl phosphine, methyl iodide, copper chloride/triphenyl phosphine, ferrous chloride/triphenyl phosphine, tungsten hexacarbonyl, rhenium pentacarbonyl and molybdenum hexacarbonyl are not caralysts for this reaction, rhodium being the only satisfactory caralyst. While rhodium gives good results, it is a very expensive catalyst, as are all Group VIII noble metals. U.S. Pat. No. 3,839,428 uses Group VIII or Group IIb metal catalysts but relatively high temperatures and pressures are employed.

My co-pending application Ser. No. 268,029 filed May 28, 1981, describes a process for the rearrangement or isomerization of methyl formate by means of a non-noble metal catalyst system comprising a molybdenum-nickel or a tungsten-nickel co-catalyst component and a promoter which is an organo-phosphorus compound or an organo-nitrogen compound. While this process involving a nickel catalyst makes possible effective rearrangement of methyl formate without requiring the use of a noble metal catalyst, it is useful to improve the reaction in terms of reaction rate and productivity without need for organic promoters.

It is accordingly the object of the present invention to provide an improved process for the manufacture of acetic acid by the rearrangement of methyl formate which requires neither high temperatures nor Group VIII noble metals and makes possible the production of acetic acid in high yields in short reaction times without needing to use organic promoters.

In accordance with the invention, conversation of methyl formate to acetic acid is carried out by using a molybdenum-nickel-alkali metal, a chromium-nickel-alkali metal or a tungsten-nickel alkali metal co-catalyst in the presence of a halide, which is suitably an iodide or a bromide, especially an iodide, and in the presence of carbon monoxide. The surprising discovery has been made that this co-catalyst system in an environment of the character indicated makes possible the rearrangement or isomerization of methyl formate not only at relatively low temperatures and pressures but with rapid, high yield production of acetic acid.

The outstanding effectiveness of the catalyst system of the process of this invention is particularly surprising in view of the experimental data reported in European published application No. 0 035 458 which shows the carbonylation of methanol to produce acetic acid in the presence of a nickel catalyst, an alkyl halide, an alkali or alkaline earth halide, and a solvent which is a tetramethylenesulfone or its derivative or an alkyl ether of a polyethylene glycol or an amide. In that publication, experiments using nickel in combination with chromium, molybdenum or tungsten showed absolutely no reaction even after two hours. It has also been observed that when nickel-based catalysts are ordinarily used in carbonylation reactions, there is a tendency for the nickel component to be volatilized and to appear in the vapors from the reaction. It has been surprisingly observed that, with the catalyst system of this invention, the volatility of the nickel is strongly suppressed and a highly-stable catalyst combination results.

Thus, in accordance with the invention, methyl formate is heated in the presence of carbon monoxide, in the presence of a halide, e.g., a hydrocarbyl halide, especially a lower alkyl halide, such as methyl iodide, and in the presence of the co-catalyst combination which has been identified above.

Carbon monoxide is removed in the vapor phase and, if desired, recycled. Normally-liquid and relatively-volatile components such as an alkyl halide, unreacted methyl formate and any by-products present in the final product mixture can be readily removed and separated from each other as by distillation, for recycling, and the net yield of product is substantially exclusively the desired acetic acid. In the case of liquid-phase reaction, which is preferred, the organic compounds are easily separated from the metal-containing components, as by distillation. The reaction is suitably carried out in a reaction zone to which the carbon monoxide, methyl formate, the halide, and the co-catalyst are fed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used by they tend to lead to reduced reaction rates, and higher temperatures may also be employed but there is no particular advantage in their use. The time of reaction is also not a paramater of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this component are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst compounds of the reaction mixture. The boiling points of the volatile components are sufficiently far apart that their separation by conventional distillation presents no particular problem. Likewise, the higher-boiling organic components can be readily distilled away from the metal caralyst components. The thus-recovered co-catalyst, as well as the halide component, can then be combined with fresh amounts of methyl formate and carbon monoxide and reacted to produce additional quantities of acetic acid.

Although not necessary, the process can be carried out in the presence of a solvent or diluent. The presence of a higher-boiling solvent or diluent, preferably the product acid itself, will make it possible to employ more moderate total pressures. Alternatively, the solvent or diluent may be any organic solvent which is inert in the environment of the process such as hydrocarbons, e.g., octane, benzene, toluene, xylene and qetralin or carboxylic acids. A carboxylic acid, if used, should preferably be acetic acid since it is preferred that the solvent employed be one that is indigenous to the system, although other carboxylic acids can also be used. A solvent or diluent, when not the product itself, is suitably selected which has a boiling point sufficiently different from the desired produce in the reaction mixture so that it can be readily separated, as will be apparent to persons skilled in the art. Mixtures can be used.

The carbon monoxide is preferably employed in substantially pure form, as available commercially, but inert diluents such as carbon dioxide, nitrogen, methane, and noble gases can be present if desired. The presence of inert diluents does not affet the carbonylation reaction but their presence makes it necessary to increase the total pressure in order to maintain the desired CO partial pressure. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those mentioned above. It has been surprisingly found that the presence of hydrogen does not lead to the formation of reduction products. The diluent gas, e.g., hydrogen, may generally be used in amount up to about 95%, if desired.

The co-catalyst components can be employed in any convenient form. For example, the nickel, molybdenum, tungsten and chromium can be the metals themselves in finely-divided form, or a compound, both organic or inorganic, which is effective to introduce these co-catalyst components into the reaction system. Thus, typical compounds include the carbonate, oxide, hydroxide, bromide, iodide, chloride, oxyhalide, hydride, lower alkoxide (methoxide), phenoxide, or Mo, W, Cr or Ni carboxylates wherein the carboxylate ion is derived from an alkanoic acid of 1 to 20 carbon atoms such as acetates, butyrates, decanoates, laurates, benzoates, and the like. Similarly, complexes of these co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, soldium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are preferred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of caralyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 15 millimoles to 500 millimoles per liter and most preferably 15 millimoles to 150 millimoles per liter.

The ratio of nickel to the molybdenum, tungsten, or chromium co-catalyst component can vary. Typically, it is one mol of the nickel component per 0.01 to 100 mols of the second co-catalyst component, i.e., the molybdenum, tungsten, or chromium component, preferably the nickel component is used in the amount of 1 mol per 0.1 to 20 mols, most preferably 1 mol per 1 to 10 mols of the second co-catalyst component. Similarly, the ratio of nickel to the alkali metal component can vary, e.g., one mol of nickel per 1 to 1000 mols of alkali metal component, preferably 10 to 100 and most preferably 20 to 50.

The amount of iodide component may also vary widely but, in general, it should be present in an amount of at least 0.1 mol (expressed as I) per mol of nickel. Typically, there are used 1 to 100 mols of the iodide per mol of nickel, preferably 2 to 50 mols per mol. Ordinarily, more than 200 mols of iodide per mole of nickel are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine. The forgoing also supplies to a bromide component when the iodide is replaced with a bromide.

As previously mentioned, the catalyst system of this invention comprises an iodide component and a molybdenum-nickel-alkali metal, tungsten-nickel-alkali metal or chromium-nichel-alkali metal co-catalyst component. The caralyst system of this invention permits the production of acetic acid in high yields in short reaction times without the use of Group VIII noble metals and the presence of the alkali metal component together with the molybdenum, tungsten or chromium component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal, tungsten-nickel-alkali metal or chromium-nickel-alkali metal iodide co-catalyst component and the component can be represented by the following formula: X:T:Z:Q, wherein X is molybdenum, tungsten or chromium, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is the alkali metal component. The preferred alkali metal is lithium as previously indicated, and being in the form of an iodide or a bromide or a carboxylate as defined for X and T, the molar ratio of X to T being 0.1–10:1, the molar ratio of X+T to Q being 0.1–10.1, and the molar ratio of Z to X+T being 0.01–0.1:1. The iodide component can be replaced with a bromide.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ *and most preferably* 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight, unless otherwise indicated.

EXAMPLE 1

A one-liter Parr autoclave was charged with 150 parts of methyl formate, 100 parts of methyl iodide, 101 parts of acetic acid, 7.5 parts of nickel iodide, 15 parts of molybdenum carbonyl, and 60 parts of lithium iodide. The reactor was flushed three times with 50 p.s.i.g. of carbon monoxide and then pressured with 70 p.s.i.g. of hydrogen and 230 p.s.i.g. of carbon monoxide. Then the reactor was heated to 200° C. and maintained at this temperature for 3 hours. The contents of the reactor were then removed and analyzed by gas chromatongraphy. Analysis shows the reaction mixture to contain a net make of 100 parts of acetic acid along with unreacted methyl formate, methyl iodide, the catalyst components and the originally-charged acetic acid.

EXAMPLE 2

The autoclave of Example 1 was charged with 150 parts of methyl formate, 100 parts of methyl iodide, 100 parts of acetic acid, 7.5 parts of nickel iodide, 15 parts of molybdenum carbonyl, and 60 parts of cesium iodide. The reactor was flushed three times with 50 p.s.i.g. of carbon monoxide and then pressured with 70 p.s.i.g. of hydrogen and 450 p.s.i.g. of carbon monoxide. Then the reactor was heated to 200° C. and maintained at this temperature for 5 hours. The contents of the reactor were then removed and analyzed by gas chromatography. Analysis showed the reaction mixture to contain a net make of 127 parts of acetic acid along with unreacted methyl formate, methyl iodide, the catalyst components and the originally-charged acetic acid.

EXAMPLE 3

The reactor of Example 1 was charged with 150 parts of methyl formate, 100 parts of methyl iodide, 100 parts of acetic acid, 7.5 parts of nickel iodide, 15 parts of chromium carbonyl, and 60 parts of lithium iodide. The reactor was flushed three times with 50 p.s.i.g. of carbon monoxide and then pressured with 70 p.s.i.g. of hydrogen and 230 p.s.i.g. of carbon monoxide. Then the reactor was heated to 200° C. and maintained at this temperature for 3 hours. The contents of the reactor were then removed and analyzed by gas chromatography. Analysis showed the reaction mixture to contain a net make of 123 parts of acetic acid along with unreacted methyl formate, methyl iodide, the catalyst components and the originally-charged acetic acid.

EXAMPLE 4

The one-liter Parr autoclave of Example 1 was charged with 150 parts of methyl formate, 100 parts of methyl iodide, 100 parts of acetic acid, 7.5 parts of nickel iodide, 15 parts of tungsten hexacarbonyl and 60 parts of lithium iodide. The reactor was flushed three times with 50 p.s.i.g. of carbon monoxide and then pressured with 70 p.s.i.g. of hydrogen and 430 p.s.i.g. of carbon monoxide. Then the reactor was heated to 200° C. and maintained at this temperature for 5 hours. The contents of the reactor were then removed and analyzed by gas chromatography. Analysis showed the reaction mixture to contain a net make of 100 parts of acetic acid along with unreacted methyl formate, methyl iodide, the catalyst components and the originally-charged acetic acid.

EXAMPLE 5

The one-liter Parr autoclave of Example 1 was charged with 150 parts of methyl formate, 100 parts of methyl iodide, 100 parts of acetic acid, 7.5 parts of nickel iodide, 15 parts of molybdenum hexacarbonyl and 60 parts of lithium iodide. The reactor was flushed three times with 50 p.s.i.g. of carbon monoxide and then pressured with 500 p.s.i.g. of carbon monoxide. Then the reactor was heated to 200° C. and maintained at this temperature for 5 hours. The contents of the reactor were then removed and analyzed by gas chromatography. Analysis showed the reaction mixture to contain a net make of 149 parts of acetic acid along with unreacted methyl formate, methyl iodide, the catalyst components and the originally-charged acetic acid. There was an essentially total conversion of the charged methyl formate.

What is claimed is:

1. A process for the preparation of acetic acid which comprises heating methyl formate with carbon monoxide in the presence of a molybdenum - nickel - alkali metal, a chromium - nickel - alkali metal or a tungsten - nickel - alkali metal co-catalyst component, and being free from organic promoters selected from the group consisting of organo-phosphorus compounds and organo-nitrogen compounds, and in the presence of an iodide or bromide.

2. A process as defined in claim 1, wherein the co-catalyst component is molybdenum-nickel-alkali metal.

3. A process as defined in claim 1, wherein the alkali-metal is lithium.

4. A process as defined in claim 3, wherein the co-catalyst component is molybdenum-nickel-lithium.

* * * * *